(12) United States Patent
Kojima et al.

(10) Patent No.: US 9,629,823 B2
(45) Date of Patent: Apr. 25, 2017

(54) COMPOSITION FOR PROMOTING COLLAGEN PRODUCTION, FOR PROMOTING ELASTIN PRODUCTION AND/OR FOR PROMOTING KERATINOCYTE MIGRATION AND USAGE THEREFOR

(71) Applicants: PUBLIC UNIVERSITY CORPORATION OSAKA CITY UNIVERSITY, Osaka-shi, Osaka (JP); KIYOMOTO IRON & MACHINERY WORKS CO LTD, Nobeoka-shi, Miyazaki (JP)

(72) Inventors: Akiko Kojima, Osaka (JP); Isao Yuasa, Osaka (JP); Kunio Kiyomoto, Nobeoka (JP); Ayano Omura, Nobeoka (JP)

(73) Assignees: Public University Corporation Osaka City University, Osaka (JP); Kiyomoto Iron & Machinery Works Co. Ltd., Miyazaki (JP)

(*) Notice: Subject to any disclaimer, the term of this patent is extended or adjusted under 35 U.S.C. 154(b) by 0 days.

(21) Appl. No.: 14/902,769

(22) PCT Filed: Jun. 2, 2014

(86) PCT No.: PCT/JP2014/064622
§ 371 (c)(1),
(2) Date: Jan. 4, 2016

(87) PCT Pub. No.: WO2015/001891
PCT Pub. Date: Jan. 8, 2015

(65) Prior Publication Data
US 2016/0175280 A1  Jun. 23, 2016

(30) Foreign Application Priority Data
Jul. 4, 2013 (JP) .................................. 2013-140751

(51) Int. Cl.
| | | |
|---|---|---|
| A61K 31/36 | (2006.01) | |
| A61Q 19/08 | (2006.01) | |
| A61K 8/49 | (2006.01) | |
| A61K 36/185 | (2006.01) | |
| A61Q 1/12 | (2006.01) | |
| A61Q 19/00 | (2006.01) | |
| A61Q 19/10 | (2006.01) | |

(52) U.S. Cl.
CPC ............ *A61K 31/36* (2013.01); *A61K 8/4973* (2013.01); *A61K 36/185* (2013.01); *A61Q 1/12* (2013.01); *A61Q 19/00* (2013.01); *A61Q 19/007* (2013.01); *A61Q 19/08* (2013.01); *A61Q 19/10* (2013.01)

(58) Field of Classification Search
CPC .............................. A61K 31/36; A61Q 19/00
See application file for complete search history.

(56) References Cited

U.S. PATENT DOCUMENTS

2006/0289834 A1   12/2006   Doisaki
2007/0166255 A1*   7/2007   Gupta .................... A61K 8/31
                                                        424/70.1

FOREIGN PATENT DOCUMENTS

| JP | Hei 10-182331 A | 7/1998 |
| JP | 2004-115495 A | 4/2004 |
| JP | 2010-001267 A | 1/2010 |
| WO | 2004-048497 A1 | 6/2004 |

OTHER PUBLICATIONS

Yamashita et al. J. Nutr. Sci. Vitaminol., 2007, vol. 53, pp. 393-399.*
Kiran, et al. "Wound healing activity of Sesamum indicum L seed and oil in rats." Indiana J. Exp. Biol., 2008, vol. 46, No. 11, p. 777-782. (See International Search Report).
Kang, et al. "Mode of action of sesame lignans in protecting low-density lipoprotein against oxidative damage in vitro." Life Science, 2000, vol. 66, No. 2, p. 161-171. (See International Search Report.).
Nizamutdinova, et al. "Anthocyanins from black soybean seed coats stimulate wound healing in fibroblasts and keratinocytes and prevent inflammation in endothelial cells." Food Chem. Toxicol., 2009, vol. 47, No. 11, p. 2806-2812. (See International Search Report.).
Japanese Patent Office, International Search Report, issued in corresponding Application No. PCT/JP2014/064622, mailed Aug. 26, 2014.

* cited by examiner

*Primary Examiner* — James D Anderson
(74) *Attorney, Agent, or Firm* — Stites & Harbison, PLLC; Mandy Wilson Decker; Sean Ritchie

(57) ABSTRACT

The present invention relates to a composition for enhancing collagen production, for enhancing elastin production and/or for enhancing keratinocyte migration, including sesaminol as an active component. The present invention also relates to a method for enhancing collagen production, for enhancing elastin production and/or for enhancing keratinocyte migration, including administering the composition.

5 Claims, 2 Drawing Sheets

COMPOSITION FOR PROMOTING COLLAGEN PRODUCTION, FOR PROMOTING ELASTIN PRODUCTION AND/OR FOR PROMOTING KERATINOCYTE MIGRATION AND USAGE THEREFOR

TECHNICAL FIELD

The present invention relates to a composition for promoting (enhancing) collagen production, for promoting (enhancing) elastin production and/or for promoting (enhancing) keratinocyte migration, including sesaminol as an active component. The present invention also relates to a method for promoting (enhancing) collagen production, for promoting (enhancing) elastin production and/or for promoting (enhancing) keratinocyte migration, including administering the composition.

BACKGROUND ART

Skin includes three layers: epidermis, dermis and subcutaneous tissue. Among these, dermis contains a high amount of collagen and elastin which are extracellular matrix components. The components are important for maintenance of skin functions such as skin elasticity and water retentivity. Collagen and elastin are produced by fibroblasts in dermis. When fibroblasts are however less functional due to stimulation by ultraviolet rays or aging, collagen and elastin in dermis are denatured or reduced the amount. As a result, skin undergoes senile change such as generation of wrinkles or sagging and reduction in skin function including water retentivity and elasticity.

Most parts of epidermis include keratinocytes. Keratinocytes grow in the basal layer, migrate into the horny layer and finally fall off as scurf. Thus the migration ability of keratinocytes is important for promotion of skin metabolism and maintenance of skin barrier function.

The ability of collagen and elastin production of fibroblasts and the migration ability of keratinocytes are also important for the wounds healing. For example, when dermis is lost due to a sever wound, granulation tissue must be generated to fill the region of the wound. The granulation tissue includes extracellular matrix such as fibroblasts and collagen produced by fibroblasts. Further, epidermis lost due to the wound is repaired by keratinocytes which migrate from the epidermal basal layer surrounding the region of the wound to cover the region of the wound.

For the purpose of prevention of senile change of skin or improvement of skin, various compositions have been developed so far including compositions containing saccharides, amino acids, organic acids and pyrrolidone carboxylic acid and compositions containing extracellular matrix components such as collagen.

Recently, attention is focused on lignans in sesame seeds which may be useful for amelioration of skin problems or suppression of skin inflammation. For example, Patent Literature 1 discloses use of sesame essential oil containing lignans as antioxidants for a composition for external use. Patent Literature 2 discloses a composition for external use containing a sesame lignan, sesamol.

CITATION LIST

Patent Literature

Patent Literature 1: Japanese Unexamined Patent Application Publication No. 2010-1267

Patent Literature 2: WO 2004/048497

SUMMARY OF INVENTION

Technical Problem

However, conventional compositions described above merely increase the moisture-retaining property of the skin to improve the condition of epidermal corneum or suppress skin inflammation, and thus are not sufficient for cosmetic purposes such as prevention of senile change of skin or improvement of skin or for wound healing. With the foregoing in view, an object of the present invention is to provide a composition which is more effective for cosmetic or wound healing purposes.

Solution to Problem

The inventors of the present invention found, as a result of extensive study, that sesaminol, a type of lignans in sesame, has abilities to enhance collagen production, to enhance elastin production and to enhance keratinocyte migration. Thereby the inventors have completed the present invention.

Thus the present invention provides a composition for enhancement of collagen production, for enhancement of elastin production and/or for enhancement of keratinocyte migration, including sesaminol as an active component.

The present invention also provides a method for enhancement of collagen production, for enhancement of elastin production and/or for enhancement of keratinocyte migration, including administering a composition containing sesaminol as an active component.

Advantageous Effects of Invention

According to the present invention, a migration ability of keratinocytes is improved and collagen and elastin production is enhanced in fibroblasts. Due to these actions, it is expected that the present invention is effective in cosmetic and wound healing.

DESCRIPTION OF EMBODIMENTS

Figure 1:
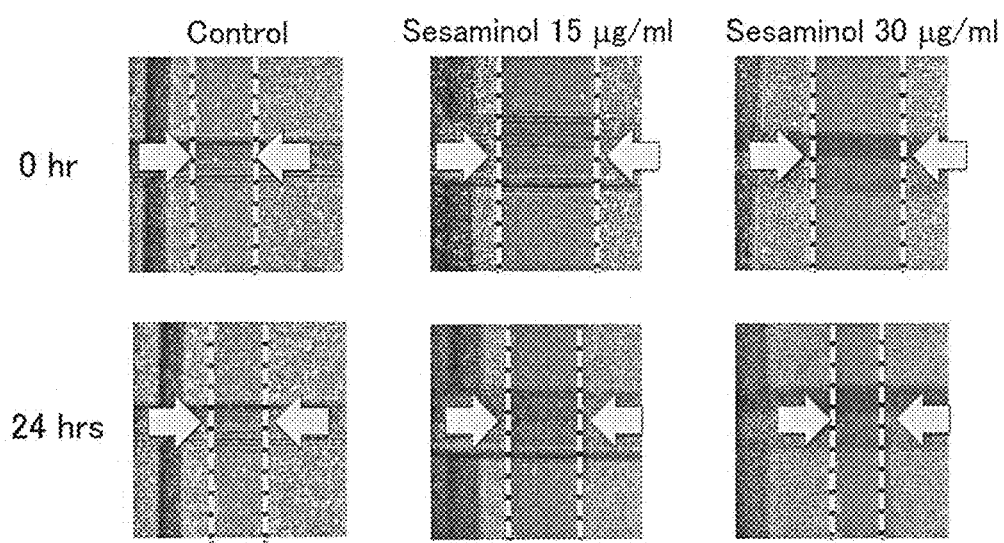
FIG. 1 is a photographic image showing the effect of sesaminol on migration ability of cells as observed by wound healing assay using human normal skin-derived keratinocyte HaCaT cells.

A composition for enhancement of collagen production, for enhancement of elastin production and/or for enhancement of keratinocyte migration of the present invention (hereinafter also merely referred to as "composition") includes sesaminol as an active component. Sesaminol is known as a lignan contained in sesame seeds and is a compound represented by the following structural formula:

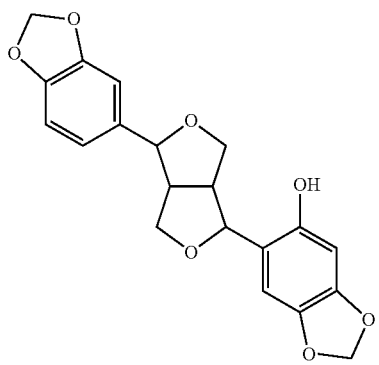 [SMILES: Oc1cc2c(cc1C1OCC3C(c4ccc5c(c4)OCO5)OCC13)OCO2]

Sesaminol used in the present invention may be derived from any source without limitation and may be sesaminol derived from plants such as sesame seeds or synthesised or semi-synthesised sesaminol. Methods per se for obtaining sesaminol from sesame seeds and the like are known and examples thereof include methods for producing sesaminol by the action of enzymes of certain microorganisms from raw materials including sesame seeds or defatted lees of the seeds (see Japanese Unexamined Patent Application Publication Nos. 2006-61115 and 2008-167712).

In the embodiments of the present invention, it is preferable to use sesaminol obtained from sesaminol glycoside in defatted lees of sesame seeds according to the method described in Japanese Unexamined Patent Application Publication No. 2008-167712. The obtained sesaminol may be directly used in the composition of the present invention or may be optionally subjected to processes such as concentration, dilution, filtration, deodorization, decolouration and drying.

In the embodiments of the present invention, the composition may only contain sesaminol; however the composition may appropriately contain other components which are generally used in the technical fields of cosmetics, quasi drug, pharmaceuticals, food or the like at an amount that does not deteriorate the action of sesaminol.

Examples of such components include oil and fat (cocoa butter, palm oil, palm kernel oil, olive oil, macadamia nut oil, castor oil, etc.), wax (beeswax, carnauba wax, jojoba oil, lanolin, etc.), a hydrocarbon (solid paraffin, petrolatum, petroleum jelly, squalene, etc.), a fatty acid (oleic acid, linoleic acid, isostearic acid, undecylenic acid, lauric acid, myristic acid, stearic acid, etc.), an alcohol (ethanol, cetyl alcohol, stearyl alcohol, isostearyl alcohol, etc.), an ester (myristyl myristate, isopropyl myristate, 2-octyldodecyl myristate, cetyl 2-ethylhexanoate, glyceryl monostearate, decyl oleate, etc.), an anionic surfactant (higher fatty acid soap, salts of alkyl sulphate esters, salts of acyl N-methyl-taurine, etc.), a cationic surfactant (alkyltrimethylammonium chloride, dialkyldimethylammonium chloride, benzalkonium chloride, etc.), an amphiphilic surfactant (alkyldimethylaminoacetate betaine, alkylamido propyldimethylaminoacetate betaine, 2-alkyl-N-carboylmethyl-N-hydroxyethyl imidazolinium betaine, etc.), a nonionic surfactant (of polyoxyethylene, of polyalcohol ester, ethylene oxide-propylene oxide block copolymers, etc.), a fragrance (synthetic fragrances, natural fragrances, etc.), a sweetener (sucrose, *stevia*, etc.), an algefacient (menthol, camphor, etc.), a pH-controlling agent (sodium hydrogen carbonate, potassium carbonate, etc.), a preservative (sodium benzoate, sorbic acid, etc.), a moisturising agent (glycerol, collagen, propylene glycol, 1,3-butylene glycol, polyethylene glycol, sorbitol, sodium lactate, sodium 2-pyrrolidone-5-carboxylate, sodium hyaluronate, plant extracts, etc.), a whitening agent (L-ascorbic acid and derivatives thereof, arbutin, hydroquinone β-D-glucose, ellagic acid, kojic acid, tranexamic acid, etc.), an anti-wrinkle agent (vitamin A and related compounds, α-hydroxy acid, etc.), an agent for improving skin problems (glycyrrhizic acid derivatives, allantoin, azulene, etc.), an acne drug (vitamin B6, salicylic acid, benzalkonium chloride, etc.), an agent for preventing underarm odour (chlorohydroxyaluminium, zinc oxide, benzethonium chloride, etc.), a styptic (aluminium chloride, tannic acid, etc.), a component for hair restoration (*Swertia japonica* extract, *Capsicum annuum* fruit extract, vitamin B1, vitamin B2, etc.), a component for preventing dandruff and itchiness (salicylic acid, vitamin B6, trichlorocarbanilide, etc.), an anti-bacterial agent (isopropyl methylphenol, paraben, benzalkonium chloride, etc.), powder (synthetic organic dyes, natural dyes, inorganic pigments, pearlescent pigments, polymer powder, etc.), an ultraviolet-absorbing agent (2-ethylhexyl para-methoxycinnamate, benzophenone derivatives, para-aminobenzoic acid derivatives, methoxycinnamic acid derivatives, salicylic acid derivatives, etc.), an ultraviolet scattering agent (titanium oxide, zinc oxide, etc.), a thickening agent (acacia gum, methylcellulose, quince seed gum, xanthan gum, gelatine, carboxymethylcellulose, carboxymethyl starch, alginates, carboxyvinyl polymers, ethylene oxide-propylene oxide block copolymers, bentonite, etc.), a film-forming agent (polyvinyl alcohol, polyvinylpyrrolidone, nitrocellulose, etc.), an antioxidant (vitamin C, vitamin E, etc.), a chelating agent (edetate disodium, sodium citrate, sodium metaphosphate, etc.), a lubricant (magnesium stearate, talc, polyethylene glycol, etc.), a disintegrating agent (starch, microcrystalline cellulose, etc.) and the like.

The composition of the present invention may be administered by any method without limitation, and the method for administration may be appropriately selected from oral administration, injection (subcutaneous, intradermal, intramuscular, intravenous, intraarterial), administration on skin, transdermal administration and the like, among which application on skin or transdermal administration is preferred. When the composition of the present invention is administered on skin, the composition is applied on skin or sprayed thereon, or a formulation containing the composition of the present invention in a releasable manner (such as adhesive skin patches, tapes and poultices) is used.

The dosage of the composition of the present invention is not particularly limited and may be appropriately selected according to the condition of the skin or wound. For example, when the composition of the present invention is ingested by an adult, the dosage thereof may be 1 to 100 mg and preferably 2 to 10 mg as the amount of sesaminol per day.

When the composition of the present invention is in the form of a composition for external use, the dosage thereof to an adult is 1 to 1000 μg and preferably 10 to 500 μg as the amount of sesaminol per day. The frequency of administration of the composition of the present invention is not particularly limited and may be once or more daily.

The composition of the present invention can be provided as a cosmetic composition for external use, more specifically a composition for external use for preventing senile change of skin and/or improving skin. Senile change of skin as used herein means generation of wrinkles and sagging caused by external stimulations such as ultraviolet rays and aging, and reduction in skin function including water retentivity, elasticity and barrier function.

The composition of the present invention can also be provided as a composition for external use for wound healing. The extent and type of wound are not particularly limited in the embodiments of the present invention. The composition of the present invention can be widely applied from a wound that can be cured by epidermal repair to a wound that requires granulation in damaged dermis.

The composition of the present invention may be in any form of a cosmetic, quasi drug, pharmaceutical drug, food or research reagent, as far as sesaminol can be administered, among which a cosmetic, quasi drug or pharmaceutical drug is preferable.

More specifically, examples of a cosmetic composition for external use include skin toners, creams, milky lotions, lotions, foundation, essence, packs, beauty masks, cleansing products, oils, lipsticks, powder, shampoos, rinses, conditioners, soaps, face washes, body soaps, bath salts, sunscreens, solutions for scalp and the like.

Examples of a composition for external use for wound healing include ointments, creams, lotions, sprays for external use, adhesive skin patches, tapes, poultices, powder for external use and the like.

The composition in the forms described above may be produced according to well-known methods in the art.

The composition of the present invention may contain any amount of sesaminol without limitation. The amount of sesaminol may be appropriately selected according to the form of the composition. For example, the amount of sesaminol relative to the total weight of the composition may be 0.0001 to 50% by weight, preferably 0.0005 to 40% by weight and more preferably 0.001 to 35% by weight.

The scope of the present invention also encompasses use of sesaminol for manufacturing a composition for enhancement of collagen production, for enhancement of elastin production and/or for enhancement of keratinocyte migration. The composition and sesaminol are as described herein above.

The scope of the present invention also encompasses a method for enhancement of collagen production, for enhancement of elastin production and/or for enhancement of keratinocyte migration, including administering a composition containing sesaminol as an active component. Sesaminol and the composition containing sesaminol as an active component are as described hereinabove. The method for administration and dosage of the composition are also as described hereinabove.

The scope of the present invention further encompasses use of sesaminol for enhancement of collagen production, for enhancement of elastin production and/or for enhancement of keratinocyte migration. Sesaminol is as described hereinabove.

The present invention is hereinafter more specifically described by way of Examples which do not limit the present invention.

EXAMPLES

Preparation Example

Preparation of Sesaminol

In this Example the sesaminol used was obtained from sesaminol glycoside contained in sesame defatted lees by culturing *Paenibacillus* sp. KB0549 strain (Accession No.: FERM P-21057) in a medium containing sesame defatted lees according to the method described in Japanese Unexamined Patent Application Publication No. 2008-167712. Specifically, sesaminol was prepared as follows.

KB0549 strain was grown in a medium containing a warm water extract of sesame defatted lees (available from Takemoto Oil & Fat Co., Ltd.), 1.0% tryptone, 0.5% yeast extract and 0.89% NaCl to obtain a KB0549 culture solution. The obtained culture solution was added to sesame defatted lees (10.0 kg; heat sterilised and adjusted to water content of 70% and pH 6.0) and subjected to fermentation in a solid fermenter at 37° C. while continuing intermittent stirring and aeration over 6 days.

The fermented sesame defatted lees were dried to have a water content of 8.5%. To the dried material, 95% ethanol was added at a proportion of 100 L per 10.0 kg of the dried material and heated to 50° C. while stirring to extract sesaminol. The resulting liquid extract was subjected to diatomaceous earth filtration by filter pressing to remove solid matters and obtain a liquid filtrate (82 L). The resulting filtrate was concentrated to 4.1 L in a vacuum concentrating apparatus. To the resulting concentrated solution, 4 times or more volume of 99.5% ethanol were added and insoluble matters were removed by filtration through a filter paper. The obtained solution was concentrated on an evaporator to give a highly concentrated sesaminol solution (4.05 L).

The resulting highly concentrated solution was analysed on a high performance liquid chromatography (HPLC) in order to identify sesaminol and sesaminol-related compounds contained therein. As a result, it was found that the concentrated solution (4.05 L) contained 18.4 g of sesaminol. HPLC analysis was carried out under the following conditions:

HPLC: HITACHI LaChrom
Column: Wakosil-II 5C18HG ($\phi$ 4.6*250 mm, Wako Pure Chemical Industries, Ltd.)
Development solvent: A: 10% acetonitrile+0.1% trifluoroacetic acid, B: 80% acetonitrile+0.1% trifluoroacetic acid, a linear gradient of B from 10% to 100% in 40 minutes.
Flow rate: 0.8 ml/min
Analysis wavelength: 280 nm The highly concentrated sesaminol solution was dissolved in dimethyl sulphoxide (DMSO) to prepare a sesaminol solution (3.0 mg/ml) to be used in Examples. The inventors of the present invention confirmed that the resulting sesaminol solution was not toxic to and did not affect viability of various cell lines used in Examples.

Example 1

Effect of Sesaminol on Migration Ability of Keratinocytes (1) Cell Culture

Cells of human normal skin-derived keratinocyte HaCaT cells were inoculated at a density of $5.0 \times 10^5$ cells/dish in a plastic dish having a diameter of 35 mm with a mark on the bottom and cultured until they reached confluence in a 5% $CO_2$ incubator at 37° C. The culture medium used was Dulbecco's modified Eagle's medium (DMEM: Nissui Pharmaceutical Co., Ltd.) containing 10% fetal bovine serum (FBS: Nichirei Biosciences, Inc.), penicillin (50 units/ml, Meiji Co., Ltd.) and streptomycin (50 mg/ml, Meiji Co., Ltd.). The medium was replaced every two days.

(2) Evaluation of Cell Migration by Scratch Assay

After culturing the cells until they reached confluence, cells in the dish were scraped with a chip and a linear wound pattern was formed therewith. Immediately thereafter, the wound pattern was analysed under an inverted microscope (OLYMPUS IX-70: Olympus Corporation) and photographed. The medium containing the sesaminol solution so as to have the final concentration of sesaminol of 15 or 30 µg/ml was added followed by incubation for 24 hours in a 5% $CO_2$ incubator at 37° C. The wound pattern was then analysed with OLYMPUS IX-70 and photographed. As a control, the scratch assay was carried out in the similar manner except that the medium without sesaminol solution was used.

(3) Calculation of Cell Migration Distance

Based on the obtained photographic images, the width of wound patterns in the samples was measured. FIG. 1 shows photographic images of the samples. Based on the measurement results, the repair rate in the region of the wound by sesaminol was calculated. The repair rates for the samples calculated are as follows with the rate for the control being 100.

Control: 100.0±34.5
Group with sesaminol addition at 15 µg/ml: 121.7±25.6
Group with sesaminol addition at 30 µg/ml: 139.1±20.6

These results indicate that addition of sesaminol increased migration of HaCaT cells compared to the control. Therefore, it is demonstrated that sesaminol has the ability to enhance keratinocyte migration.

Example 2

Effect of Sesaminol on Collagen Enhancing Ability of Fibroblasts (1) Cell Culture Cells of human normal skin-derived fibroblast CCD-10595K strain (purchased from DS Pharma Biomedical Co., Ltd.) were inoculated at a density of $3.0 \times 10^4$ cells/ml in a plastic dish having a diameter of 35 mm and cultured in a 5% $CO_2$ incubator at 37° C. The medium used was the same medium as in Example 1. After 1 or 2 days, the medium was replaced with the medium containing the sesaminol solution so as to contain sesaminol at a final concentration of 15 or 30 µg/ml and the cells were incubated for 24 hours in a 5% $CO_2$ incubator at 37° C. As a control, incubation was carried out using the medium without sesaminol solution.

(2) Evaluation of Collagen Production by Immunohistochemistry

Figure 2:
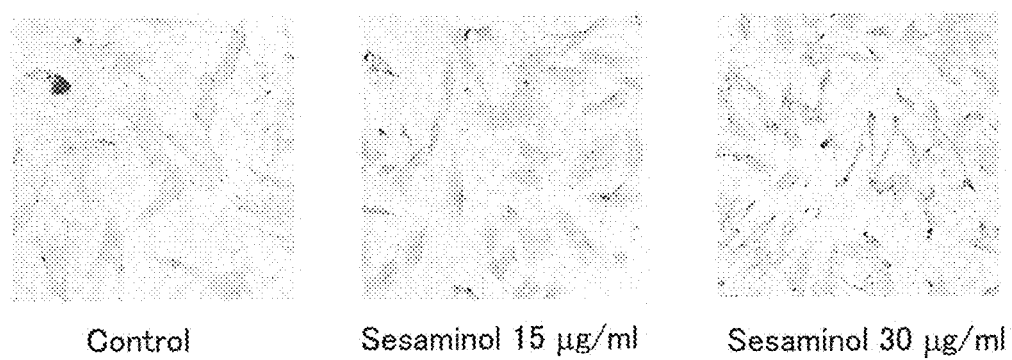
FIG. 2 is a photographic image showing the effect of sesaminol on collagen producing ability of cells as observed by immunohistochemical analysis using human normal skin-derived fibroblasts, CCD-10595K cells.

After the incubation, cells were washed three times with PBS. Cells were then fixed in 4% paraformaldehyde and stored overnight at 4° C. The fixed cells were treated with 0.1% Triton®-X100 diluted in PBS for 5 minutes and washed with PBS for 5 minutes. The treated cells were blocked in 3% $H_2O_2$ and washed with PBS for 5 minutes. The cells were further blocked in 10% normal goat serum and washed with PBS for 5 minutes. A rabbit anti-type I collagen antibody (LSL) diluted 200-fold in PBS was added to the cells on a slide glass which were then incubated for 1 hour and washed with PBS for 5 minutes. A biotin-conjugated anti-rabbit IgG antibody (Dako A/S) diluted 400-fold in PBS was added to the cells which were then incubated for 30 minutes and washed with PBS for 5 minutes. Streptavidin-conjugated HRP (Dako A/S) diluted 400-fold in PBS was then added to the cells which were then incubated for 30 minutes and washed with PBS for 5 minutes. The cells were added with a DAB solution (3,3'-diaminobenzidine tetrahydrochloride (30 mg), distilled water (75 ml), 0.2 M PBS (75 ml), 30% $H_2O_2$ (100 µl) and 8% nickel chloride (1 ml)) and incubated for 5 minutes. The cells were then washed with PBS for 5 minutes, and a small amount of water-soluble mounting medium (Aquatex, MERCK) was applied on the cover glass which was then attached on a slide glass slide. The prepared slide was analysed on OLYMPUS IX-70 and images of stained cells were obtained. FIG. 2 shows the images.

From FIG. 2, it was found that CCD-10595K cells treated with sesaminol were stained more intensely than the control. This indicates that the addition of sesaminol increased the amount of collagen. These results demonstrate that sesaminol has the ability to promote collagen production in fibroblasts.

Example 3

Effect of Sesaminol on Collagen and Elastin Producing Ability of Fibroblasts (1) Cell Culture Cells of human normal skin-derived fibroblast CCD-10595K cells (purchased from DS Pharma Biomedical Co., Ltd.) were inoculated in a plastic dish having a diameter of 35 mm and cultured until they reached confluence in a 5% $CO_2$ incubator at 37° C. Thereafter, the medium was replaced with the medium containing the sesaminol solution so as to contain sesaminol at a final concentration of 15 or 30 µg/ml and the cells were incubated for 24 hours in a 5% $CO_2$ incubator at 37° C. The medium used was the same medium as in Example 1. The medium was replaced every two days until the cells reached confluence. As a control, incubation was carried out using the medium without sesaminol solution.

(2) Evaluation of Collagen and Elastin Production by Western Blot Analysis

After the incubation, cells were washed twice with PBS and collected into a 1.5-ml tube using a cell scraper. The tube was centrifuged (15000 rpm, 4° C., 15 seconds) to remove the supernatant and recover the precipitate (cells). To the recovered cells, an appropriate amount of lysis buffer (1% NP-40 and 1% Triton®-X100, 1 mM PMSF, 10 µg/ml leupeptin and 10 µg/ml aprotinin) was added and the tube was voltexed. The tube was cooled on ice for 30 minutes followed by ultrasonic treatment (4 cycles of 3-minute treatment and 20-second interval) to disrupt cells. The tube was centrifuged (15000 rpm, 4° C., 20 minutes) and a supernatant containing soluble cell lysate was collected. An aliquot of the collected supernatant was subjected to protein quantification using Serva Blue G (Serva Electrophoresis GmbH) based on the absorbance at 595 nm in order to calculate the amount of sample applied to electrophoresis.

Equal volumes of the supernatant containing cell lysate and a sample buffer were mixed and heated at 90° C. for 5 minutes to prepare a sample for electrophoresis. The obtained sample was subjected to electrophoresis and transfer onto a PVDF membrane according to standard methods. The membrane after transfer was blocked with 5% skimmed milk and then subjected to reaction with the primary antibody indicated below followed by washing in PBS for 5 minutes. The membrane after reaction with the primary antibody was then subjected to reaction with the secondary antibody indicated below and washed in PBS for 5 minutes. The membrane was then subjected to reaction in a DAB solution (3,3'-diaminobenzidine tetrahydrochloride (10 mg), distilled water (1 ml), 0.2 M PBS (50 ml) and 30% $H_2O_2$ (100 µl)), dried and then subjected to quantification of intensity of bands using Scion Image (free software: Scion).

The ratio of the band intensity of type I collagen or elastin relative to the band intensity of β-actin was calculated for the samples.

Primary and secondary antibodies used in the present Example are as follows:

(Primary Antibodies)

Rabbit anti-COL1A antibody (C-18) (sc-8784-R: Santa Cruz)

Mouse anti-elastin antibody (*Acris* Antibodies GmbH)

Mouse anti-human smooth muscle actin antibody (1A4) (Dako A/S)

(Secondary Antibodies)

Biotin-conjugated anti-rabbit IgG antibody (Dako A/S)

Biotin-conjugated anti-mouse IgG antibody (Dako A/S)

Figure 3:
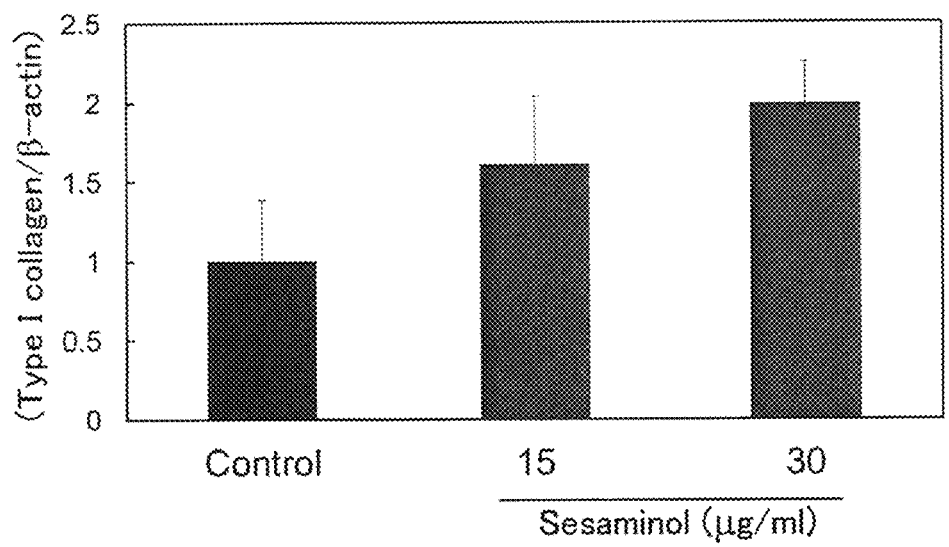
FIG. 3 is a graph showing the effect of sesaminol on collagen producing ability of cells as measured by western blot analysis using CCD-10595K cells.
Figure 4:
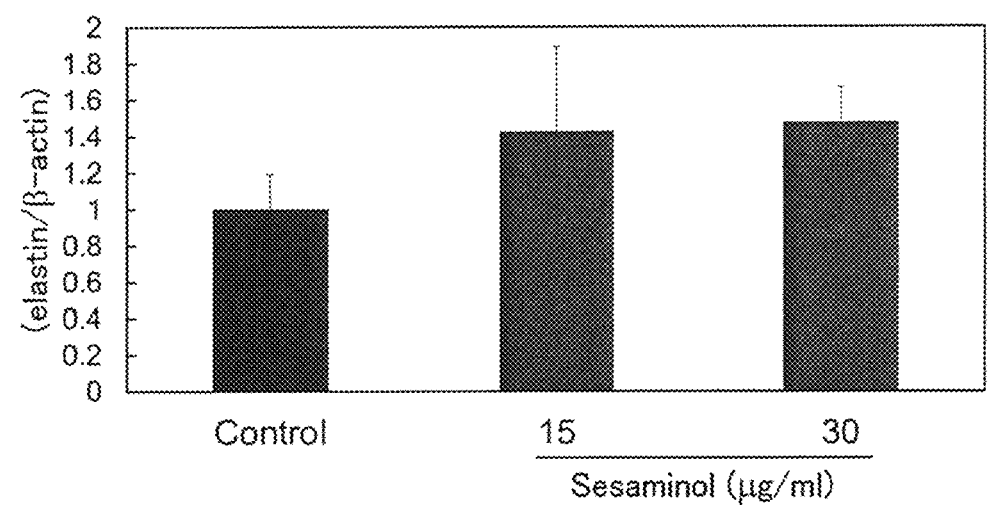
FIG. 4 is a graph showing the effect of sesaminol on elastin producing ability of cells as measured by western blot analysis using CCD-10595K cells.

The results are shown in FIGS. 3 and 4. In FIGS. 3 and 4, the ratio in cells to which sesaminol was added is represented with the ratio in control cells being 1. From FIGS. 3 and 4, it is found that expression levels of collagen and elastin were increased by addition of sesaminol. Therefore, it is demonstrated that sesaminol has the ability to enhance collagen and elastin production in fibroblasts.

Formulation Examples

Formulation Examples of the composition of the present invention are described hereinbelow. Sesaminol used is the one obtained by the method described in Preparation Example as above. In the following Formulation Examples, the amounts of components are denoted by "% by weight".

Formulation Example 1

Cream

A cream is prepared as follows. Components indicated in (A) are mixed and the mixture is heated at 80° C. Separately, components indicated in (B) are mixed and the mixture is heated at 80° C. To the mixture of (A), the mixture of (B) is gradually added while stirring to emulsify followed by cooling to 35° C. to give a cream.

| (A) | |
|---|---|
| Squalene | 15.00 (% by weight) |
| Octyldodecyl myristate | 4.00 |
| Hydrogenated soybean phospholipid | 0.20 |
| Butyl alcohol | 2.40 |
| Hydrogenated oil | 1.50 |
| Stearic acid | 1.50 |
| Lipophilic glyceryl monostearate | 1.50 |
| Polyglyceryl monostearate | 0.50 |
| Behenyl alcohol | 0.80 |
| Polyglyceryl monomyristate | 0.70 |
| Bleached beeswax | 0.30 |
| d-δ-Tocopherol | 0.05 |
| Methylparaben | 0.30 |
| Sesaminol | 1.00 |
| (B) | |
| C10-30 alkyl-modified carboxyvinyl polymer | 0.20 |
| Carboxyvinyl polymer | 0.10 |
| 1,3-Butanediol | 18.00 |
| Sodium hydroxide | 0.10 |
| Purified water | 51.85 |
| (Total: 100.00) | |

Formulation Example 2

Skin Toner

A skin toner is prepared as follows. Components indicated in (A) are mixed and the mixture is heated at 80° C. to mix and homogenise followed by cooling. Components indicated in (B) are then sequentially added at 35° C. to mix and homogenise in order to obtain a skin toner.

| (A) | |
|---|---|
| Squalene | 0.40 (% by weight) |
| Polyglyceryl monolaurate | 0.10 |
| Long chain α-hydroxy fatty acid | 0.01 |
| Glycerol | 3.00 |
| 1,3-Butylene glycol | 8.00 |
| Sesaminol | 1.00 |
| (B) | |
| Phenoxyethanol | 0.20 |
| 1,3-Butylene glycol | 10.00 |
| Allantoin | 0.10 |
| Citric acid | 0.01 |
| Sodium diethylenetriaminepentaacetate solution | 0.05 |
| Succinyl collagen solution | 0.01 |
| Purified water | 77.12 |
| (Total: 100.00) | |

The present application relates to Japanese Patent Application No. 2013-140751 filed on 4 Jul. 2013, of which Claims, Specification, Drawings and Abstract are entirely incorporated herein by reference.

The invention claimed is:

1. A method for enhancing collagen production, for enhancing elastin production and/or for enhancing keratinocyte migration, comprising administering to the skin of a human adult subject having a wound and/or senile change of skin a composition consisting essentially of sesaminol as an active component, whereby the enhancing collagen production, enhancing elastin production and/or enhancing keratinocyte migration is in the skin of the human adult subject, and wherein the dosage of sesaminol is 10 to 500 μg per day.

2. The method according to claim 1, wherein the composition is in a form of a cosmetic, quasi drug or pharmaceutical drug.

3. The method according to claim 2, wherein the cosmetic is a skin toner, cream, milky lotion, lotion, foundation, essence, pack, beauty mask or cleansing product.

4. A method for wound healing, comprising administering a composition for external use consisting essentially of sesaminol as an active component to skin of a human adult subject having a wound, whereby the enhancing keratinocyte migration is in the skin of the human adult subject, and wherein the dosage of sesaminol is 10 to 500 μg per day.

5. A method for preventing senile change of skin and/or for improving skin, comprising administering a composition for external use consisting essentially of sesaminol as an active component to skin of a human adult subject having senile change of skin, whereby the enhancing keratinocyte migration is in the skin of the human adult subject, and wherein the dosage of sesaminol is 10 to 500 μg per day.

* * * * *